US012544585B2

(12) United States Patent
Gerstenmeier

(10) Patent No.: US 12,544,585 B2
(45) Date of Patent: Feb. 10, 2026

(54) STRUCTURE FOR THERAPEUTIC APPLICATIONS

(71) Applicant: JK-HOLDING GMBH, Windhagen (DE)

(72) Inventor: Jürgen Gerstenmeier, Windhagen (DE)

(73) Assignee: JK-HOLDING GMBH, Windhagen (DE)

( * ) Notice: Subject to any disclaimer, the term of this patent is extended or adjusted under 35 U.S.C. 154(b) by 213 days.

(21) Appl. No.: 17/820,658

(22) Filed: Aug. 18, 2022

(65) Prior Publication Data

US 2022/0395696 A1 Dec. 15, 2022

Related U.S. Application Data

(63) Continuation of application No. PCT/IB2021/051328, filed on Feb. 17, 2021.

(30) Foreign Application Priority Data

Feb. 18, 2020 (CH) .................................... 00176/20

(51) Int. Cl.
*A61N 5/06* (2006.01)

(52) U.S. Cl.
CPC ........ *A61N 5/06* (2013.01); *A61N 2005/0651* (2013.01)

(58) Field of Classification Search
CPC .... A61H 2201/1654; A61H 2201/5061; A61H 2201/5064; A61H 2201/5082
See application file for complete search history.

(56) References Cited

U.S. PATENT DOCUMENTS

| | | | | |
|---|---|---|---|---|
| 4,976,256 | A | 12/1990 | Marlin et al. | |
| 6,210,351 | B1 | 4/2001 | Korenaga | |
| 7,311,683 | B2 * | 12/2007 | Turell | A61H 33/6089 601/55 |
| 2003/0212352 | A1 * | 11/2003 | Kahn | A61H 1/008 601/103 |
| 2015/0320352 | A1 | 11/2015 | Ben Shalom et al. | |

(Continued)

FOREIGN PATENT DOCUMENTS

| | | | |
|---|---|---|---|
| CN | 101460088 | A | 6/2009 |
| CN | 106580650 | A | 4/2017 |
| CN | 107432613 | A | 12/2017 |

(Continued)

OTHER PUBLICATIONS

China National Intellectual Property Administration, First Office Action issued in CN Application 202180020158.3, mailed Jul. 16, 2024. 21 pages (w/translation).

(Continued)

*Primary Examiner* — Carl H Layno
*Assistant Examiner* — Maria Catherine Anthony
(74) *Attorney, Agent, or Firm* — HESLIN ROTHERNBER FARLEY & MESITI P.C.

(57) ABSTRACT

Disclosed is a structure for therapeutic applications comprising at least one layer with sensor elements and heating elements. A first force affects the layer from one side and a second force affects the layer from the other side. The forces are detectable. The sensor elements can comprise, for example, position sensors, pressure sensors, and temperature sensors.

22 Claims, 5 Drawing Sheets

(56) References Cited

U.S. PATENT DOCUMENTS

| | | | |
|---|---|---|---|
| 2019/0290132 | A1 | 9/2019 | Au |

FOREIGN PATENT DOCUMENTS

| | | | | | |
|---|---|---|---|---|---|
| CN | 208864764 | U | | 5/2019 | |
| CN | 109925583 | A | | 6/2019 | |
| CN | 110638622 | A | | 1/2020 | |
| JP | 04500329 | A | | 1/1992 | |
| JP | 2001-333955 | A | | 12/2001 | |
| JP | 2002162048 | A | | 6/2002 | |
| JP | 2004208746 | A | | 7/2004 | |
| JP | 2007105385 | A | | 4/2007 | |
| JP | 2007325712 | A | | 12/2007 | |
| JP | 2013244177 | A | * | 12/2013 | |
| KR | 20060037727 | A | * | 5/2006 | ........... A61H 39/002 |
| KR | 101310516 | B1 | | 10/2013 | |
| TW | 201946511 | A | | 12/2019 | |
| WO | WO1990015585 | A1 | | 12/1990 | |
| WO | 2007141680 | A1 | | 12/2007 | |
| WO | 2010101633 | A3 | | 9/2010 | |
| WO | 2012055029 | A1 | | 5/2012 | |
| WO | 2019076459 | A1 | | 4/2019 | |

OTHER PUBLICATIONS

Japan Patent Office, Notice of Reasons for Rejection issued in JP Application 2022-549308, mailed Oct. 1, 2024. 8 pages (w/translation).

United Arab Emirates Ministry of Economy, First Office Action, no date provided. 9 pages.

China National Intellectual Property Administration; Notice of Allowance, Mar. 31, 2025. 8 pages (w/translation).

* cited by examiner

STRUCTURE FOR THERAPEUTIC APPLICATIONS

CROSS REFERENCES TO RELATED APPLICATIONS

This application is based on, and claims priority to: PCT Patent Application No. PCT/IB2021/051328, filed on Feb. 17, 2021 and published as PCT Publication No. WO2021/165845A1; and Swiss Patent Application No. CH 00176/20, filed on Feb. 18, 2020. The contents of the prior patent applications are hereby incorporated by reference herein in their entirety.

TECHNICAL FIELD

The present invention relates to a structure for therapeutic applications, in particular, to a layered structure for wellness, relaxation, or fitness, all according to the preambles of the independent claims.

TECHNOLOGICAL BACKGROUND

Therapeutic applications are offered as treatments to patients for medical or relaxation purposes. Massages are ideal therapies for patients suffering from stress, muscular tension and back pain. Therapeutic whole body or partial body massages using targeted forces in order to relax the muscles to soothe stiffness or cramps and to relive back and joint pain, muscle tension, muscular imbalances, stress-related muscular tension, or cervical migraine. Beneficial warmth may stimulate the entire metabolism. Help can be achieved for example by dry water massages.

Dry water massage or other water devices are known. These are devices that usually perform effective massage treatment automatically. Separated from the water by a rubber mat, a patient lies on warm water. From nozzles, which can be moved, water jets are pumped from below against the rubber mat on which the patient is lying. A treatment with a certain pressure and a treatment time of approximately 1 min to 45 min can be set individually via a keyboard or via chip cards with fixed or pre-programmed programs. Fixed massage functions, defined massage areas and massage courses can be defined and called up accordingly. Storage on a chip card is possible. The water temperature can usually be adjusted in steps from approx. 20° C. to 40° C.

During an application, the warmth of the water radiates into deep tissue layers and promotes the blood circulation of the patient. The power of the water activates the metabolism, loosens the muscles, releases tension and hardenings. An advantage of this special therapy is that it is carried out without stressing the circulation or after-sweating.

The concept of dry water massage can be used for therapy and prevention. The following therapeutic demands are made on such devices: pain relief, muscle relaxation, elimination of muscular imbalances, increase or decrease of muscle tone, local increase of blood circulation and metabolism, loosening of subcutaneous cell tissue, venous and lymphatic decongestion, reflective relief of pain, loosening of scar tissue, activation or attenuation of the vegetative nervous system, increase of the efficiency of subsequent therapeutic measures.

These requirements are achieved by the massage effect of the water jets, which produce the massage effect from one or more jets under the patient support, and by the warming effect.

The massage effect of the water and the heat transfer via the patient support to the patient represents a considerable enrichment in the treatment of back pain patients.

Compared to underwater massage, overwater or dry water massage systems or devices have the advantage that the patient does not have to go into the water and therefore does not have to remove bandages, gauze bandages, etc.

The patient support is provided by a mat made of a coextruded natural rubber material. There are problems with the surface quality and there are certain limits to the strength.

In general, there is a need for advancements in this field of technology.

SUMMARY OF THE INVENTION

It is an object of the invention to provide a structure or support for therapeutic applications. It is another object of the invention to provide a method of forming such a structure. It is a further object of the invention to provide a mat with improved properties for therapeutic applications. It is yet another object of the invention to provide an improved hydromassage device.

At least one of these objects is achieved by the features according to the independent claims. Further particular embodiments are indicated in the dependent claims and the description.

A first aspect of the invention relates to a structure for therapeutic applications that comprises at least one layer with sensor elements and may comprise heating elements. A first force affects the layer from one side and a second force affects the layer from the other side. Different forces are applied from the two sides.

In a further aspect of the invention a mat is provided that comprises the structure. The mat can be used for various therapeutic applications, for example, for wellness, relaxation, sport or fitness applications.

Another aspect of the invention relates to a hydromassage device with a movable jet or jets. The device comprises a frame and the structure that is arranged as area of support, for instance as reclining surface substantially horizontally, on one side and for receiving the moveable jet or jets from the other side.

In the context of the present invention a hydromassage device shall be understood as comprising all types of devices that provide a kinetic force through the means of a medium onto a body or body part for therapeutic or wellness purposes. The medium is preferably a fluid which can be propelled for instance as a jet towards the body or body part. In a particularly preferred embodiment, the present invention relates to devices employed for physical therapy and physical stimulation through kinetic force, encompassing impulses onto, kneading, working and/or impacting a body or body part with a jet. In a particularly preferred embodiment, the fluid comprises water or essentially consists of water.

Further in the context of the present invention the mat is to be understood as a mat being placed between a source of the kinetic force of the medium and the recipient, i.e. the body or body part. Therefore, a part at least of said kinetic is transmitted onto the body or body part through the mat. In a particularly preferred embodiment, the medium, in particular the fluid, is completely contained and the mat presents a contact surface of a therapeutic device according to the present invention with which the body or body part can be made to receive the kinetic force applied by the medium.

The sensor elements are arranged such that the first and second forces are detectable. The first force is generally created through contact by a patient or person laying, sitting, or standing on the structure; thus, the first force can be considered generally created through gravity or pressure. In other words, the patient or a user at or on the structure creates a certain pressure from one side, for instance from the top. In this example, the pressure of the first force is created by the weight of the user. In general, the first force is created through physical contact between a patient and the structure.

In a particular embodiment the sensor elements enable detection of a position. This can be achieved for instance by the sensor elements comprising position or positioning sensors as these can be used to detect user features, such as body shape or size. With that a body contour recognition and body outline or shape detection can be achieved which can be used for individual user adapted therapeutic applications. Alternatively, or additionally, the position detection can be achieved by a force sensing.

The second force is generally created through pressure to the patient or person laying or sitting on or at the structure. In other words, the user on or at the structure receives pressure forces to parts of the body, usually from the bottom. This pressure of the second force is a jet-pressure force created by a jet, preferably a water jet with a treatment pressure of 0.5-4.0 bar. The jet-pressure can be created by nozzles. From such nozzles, which can be moved in the same longitudinal movement and in some embodiments independently or in the same way, water jets are pumped from below against the structure on which the patient or user is lying. Thus, in a particular embodiment, the sensor elements comprise pressure sensors that detect impact forces such as the jet-pressure. Together with the detected body shape or size, the jet-pressure can be controlled and adapted. Further, with the detection of the body shape or size, an individual user can be identified, and, based on a predetermined therapy scheme, a respective program can be applied. This can lead to the nozzles being targeted with a defined jet-pressure to such parts of the body where a treatment is most effective. An intensity can be adjusted and controlled accordingly.

In a particular embodiment, the sensor elements comprise sensors capable of sensing a temperature and/or a temperature change. This can be achieved by temperature sensors, for instance. In a particular embodiment, the temperature sensor comprises a sensing means selected from the group consisting of negative temperature coefficient (NTC) thermistor, resistance temperature detector (RTD), thermocouple and semiconductor-based sensing.

When the sensor elements comprise temperature sensors a temperature can be sensed and measured. This can further support regulation of the temperature by a therapeutic device. The temperature can be adjusted by activating or deactivating one or more heating elements, for instance by means of a control logic and/or processing unit.

For example, a water heating system can be incorporated in a therapeutic device, either as being part of the structure and/or as being part of a medium, such as the fluid. The heating can then for instance be more uniformly dispensed because the heating system is integrated into the structure or mat in an energy-saving manner. This can also help at reducing cooling efforts of the entire device. The entire water in the frame does not need to be heated which saves electrical energy. The heating within the structure or mat is not only more comfortable for the user, the controlling and influencing with the help of the temperature sensors is also faster. That means a desired temperature can be achieved and provided quicker with-out the need to heat massive volumes of water.

With the arrangement of the sensor elements various functions such as position recognition or size recognition of the user can be realized. An automatic adjustment of the travel paths of the jet, pressure recognition and control of the water jet could be realized by means of corresponding sensors in the structure or mat. Also, only certain areas can be heated. Alternatively, various areas or portions might be heated to different temperatures.

The sensor elements can be arranged in different layers. This has the advantage that sensors of the same type are positioned within one layer whereas other sensors are within further layers. It might also be advantageous to arrange different sensors and/or heating elements within the same layer, such that the structure can be kept thin.

If the at least one layer comprises light emitting diodes (LEDs) then light effects can be created that help to guide a patient on the correct positioning. The LEDs can make the application or the device more attractive. The LEDs can be arranged within the same layer as the sensor and/or heating elements thereby reducing the thickness of the structure. However, the LEDs can also be arranged in different layers for production or effect purposes. With the help of the LEDs signals or instructions can be given to the users, e.g. to move or to change position. This might be advantageous if a patient is enjoying music or sounds via a headphone or other sound sources that should not be interrupted by voice or sound signals. The light effects might signal a certain progress or the end of the therapeutic application.

The structure may comprise electrical connections for electrical signals. The signals can be transferred from the structure to a separate or integrated controller. Such a controller unit may process the signals from the various sensors with respect to pressure or temperature. The electrical connections might have different thicknesses. The electrical connections to the heating elements might be thicker to allow a suitable current for the heating purposes.

If the structure comprises different fibres or threads, including optical fibres, desired properties can be achieved, e.g. colour or stability. For example, when the structure consists of a fabric into which the different fibres are woven together in several layers, then corresponding properties such as density, tensile strength, or OF properties can be achieved. In addition, position sensors, pressure sensors, heating elements, LEDs, etc. with the corresponding electrical connections can be integrated into the fabric to create a kind of smart mat. The strength of the mat with certain elastic fibres could be increased considerably.

Optical waveguides or optic fibres in the structure could be used for light effects, but also for detection and measurement.

The structure or mat can be arranged between at least a body part of a user and an impacting force. If the structure is thin a direct transfer of the massage or jet forces to and into the body parts is achievable. Different massage types can be provided through the structure or mat, such as parallel massage, mirror image massage, circle massage, or parallel stroke massage.

If the at least one layer is sandwiched between an upper layer and a lower layer, then the one layer is protected by the upper and lower layers. More than three layers might be advantageous, depending on the applications and use.

When the lower layer comprises an elastic waterproof film, the structure is protected and a patient on the structure or support remains dry. If the layer does not leave or leak though any water and possess waterproof properties, the overlaying layers can have electrical connections to lead electrical signals and current in order to function without any short circuit.

According to another aspect a method of forming a structure for therapeutic applications is provided. The method comprises the steps of weaving a plurality of fibres into a fabric and adding sensor elements and heating elements between the fibres to form at least one layer that is affectable or influenceable with a first force from one side and a second force from the other side. The sensor elements can detect different forces.

A further aspect of the invention relates to a method for operating a therapeutic device comprising the structure with the steps of providing a processing unit with sensor data indicative of a first force affecting a layer from one side and with sensor data indicative of a second force affecting the layer from the other side, providing at least one means for applying the second force to the layer, and adapting the second force reflective of the sensor data indicative of the first force affecting the layer from one side and the sensor data indicative of the second force affecting the layer from the other side.

The means for applying the second force to the layer is preferably a jet and the second force is a jet-pressure force created by the jet, in particular by a water jet with a treatment pressure.

The first force can be created through a physical contact between a patient and the structure.

A body shape or size of a patient can be identified by means of sensor data indicative of a first force, and, based on a predetermined therapy scheme, a respective program can be applied, in particular whereby an adapting the second force comprises a targeting nozzles to parts of the body of the patient based on a body shape or size identified.

The adapting can comprise an adjusting and controlling of an intensity of the second force dependent on the sensor data indicative of the first force affecting the layer from one side and the sensor data indicative of the second force affecting the layer from the other side.

BRIEF DESCRIPTION OF THE DRAWINGS

In order to facilitate better understanding of the present invention, reference is made below to the drawings. These show only exemplary embodiments of the subject matter of the invention.

In the figures and the associated description, identical or functionally analogous parts or elements are provided with the same reference numerals. The same or identical signs or symbols denote the same or identical elements.

DETAILED DESCRIPTION

Figure 1:
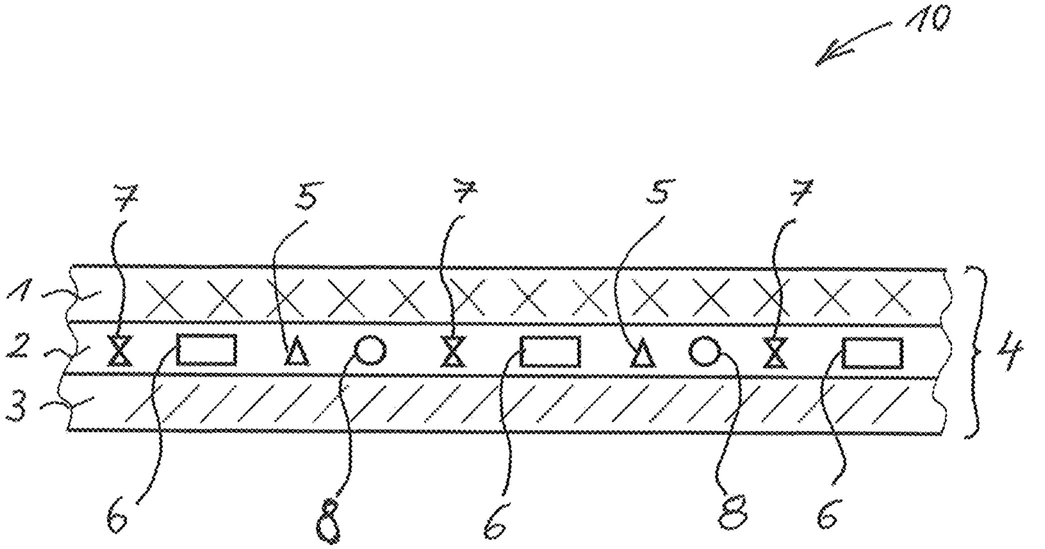
FIG. 1 Shows a schematic representation of a structure.

FIG. 1 shows a cross section of a structure 10 for therapeutic applications. The structure 10 comprises an upper layer 1, a middle layer 2, and a lower layer 3. The structure 10 is formed as a mat 4 that has certain characteristics. The three-layer woven mat 4 contains various fibres in different layers. The upper layer 1 is a resist or protective coating. The middle layer 2 comprises various sensor elements 5, 6, 7. In the same layer are arranged position sensors 5, pressure sensors 6, temperature sensors 7, and heating elements 8. All sensors and elements have electrical or other connections (not shown). The lower layer 3 comprises an insulating coating. As illustrate in the figure the middle layer 2 is sandwiched between the upper layer 1 and the lower layer 3.

In an embodiment of the present invention different fibres, also referred to as threads, are woven together in the several layers 1, 2, 3 in order to achieve respective properties, e.g. to achieve tightness, tensile strength, or a respective structure or colour. Advantageously, the position sensors 5, the pressure sensors 6, and the heating elements 8 are integrated into the fabric that results in the mat 4 with the appropriate connections in order to create a kind of smart mat. Each layer 1, 2, 3 may have a certain thickness, preferably in the range of millimetres to some centimetres.

Figure 2:
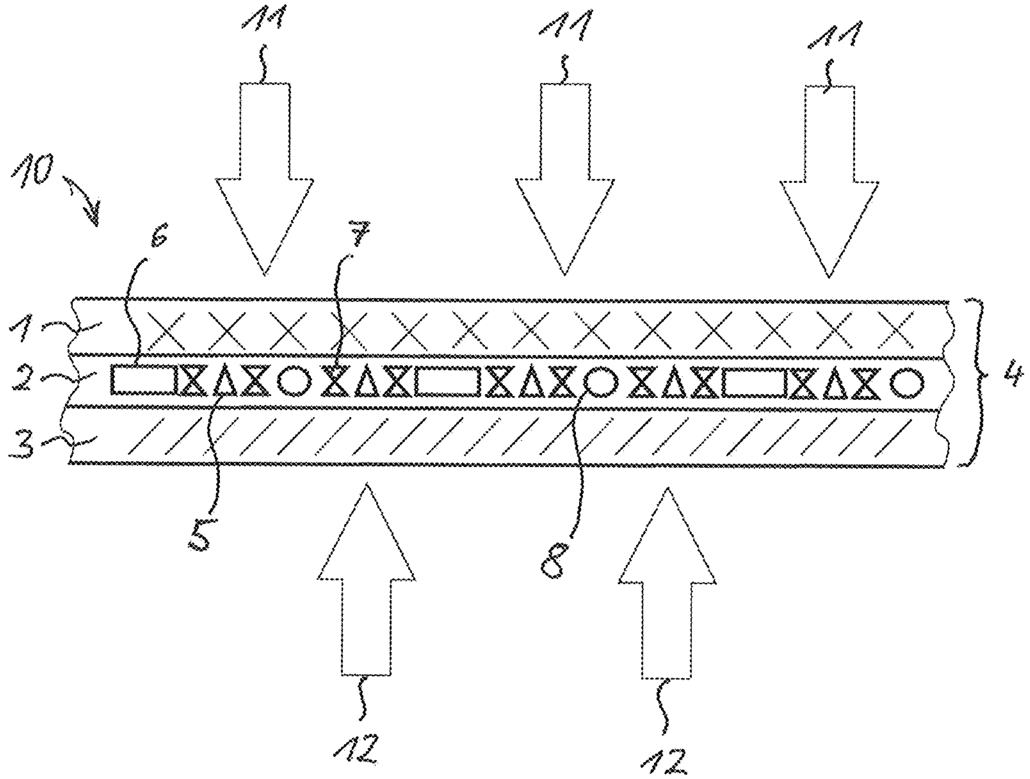
FIG. 2 Shows a further schematic representation of the structure with impacting forces.

FIG. 2 shows a further embodiment of structure 10 with the upper layer 1, the middle layer 2, and the lower layer 3, but with a modified arrangement of the elements, i.e. sensor elements 5, 6, 7 and heating elements 8. The structure 10 forms the mat 4. The middle layer 2 comprises the various sensor elements 5, 6, 7 and the heating elements 8.

Forces 11, 12 may act from both sides on the mat 4 and thus particularly on the middle layer 2. From the top first forces 11 act on the middle layer 2. From the bottom second forces 12 act on the middle layer 2. It is noted that the forces 11, 12 influence and act on all layers of the mat 4, but the detection of the forces takes place by the sensor elements 5, 6 in the middle layer 2. The sensor elements 5, 6 are arranged such that the first and second forces 11, 12 are detectable. The arrangement of the sensor elements 5, 6, 7 and heating elements 8 may follow a certain pattern. It is particularly favourable to arrange more position sensors 5 in areas where a patient is potentially reclined, whereas areas, e.g. at the edges or corners can be omitted or the density of the position sensors 5 can be reduced. Electrical signals are sent or transmitted via electrical connections to and from a control unit or central processing unit (not shown in FIG. 2).

The first force 11 is created through gravity by a patient or person laying or sitting on the mat 4. In general, a user on the mat 4 creates a certain pressure from the top. This pressure is created by weight of the user.

By measuring the pressure of the first forces 11 the exact position of a user can be determined. That means, that user features like the size or body contour of the user can be determined, and an application to the user can be applied and adapted accordingly. Individual user adapted therapeutic applications can be offered which are tailor made for specific needs or desires of a user.

The second force 12 results from a massage instrument or device with a moving drum or a jet. Such impact forces are detected by the pressure sensors 6. Electrical signals from the pressure sensors 6 are sent via the electrical connections to the control unit or central processing unit (shown in FIG. 8). In general, the second force 12 is a force that acts from the outside on the mat 4 and consequently to a patient on the mat 4. The second force or forces 12 are created and applied for the therapeutic effect, e.g. massage effect.

The temperature sensors 7 help to determine and measure the temperature at the middle layer 2. The temperature sensors 7 send electrical signals via the electrical connections to the control unit or central processing unit for processing. The heating elements 8 are heated accordingly, i.e., based on the detected and measured temperature the heating elements 8 are activated to heat up the mat 4.

Figure 3:
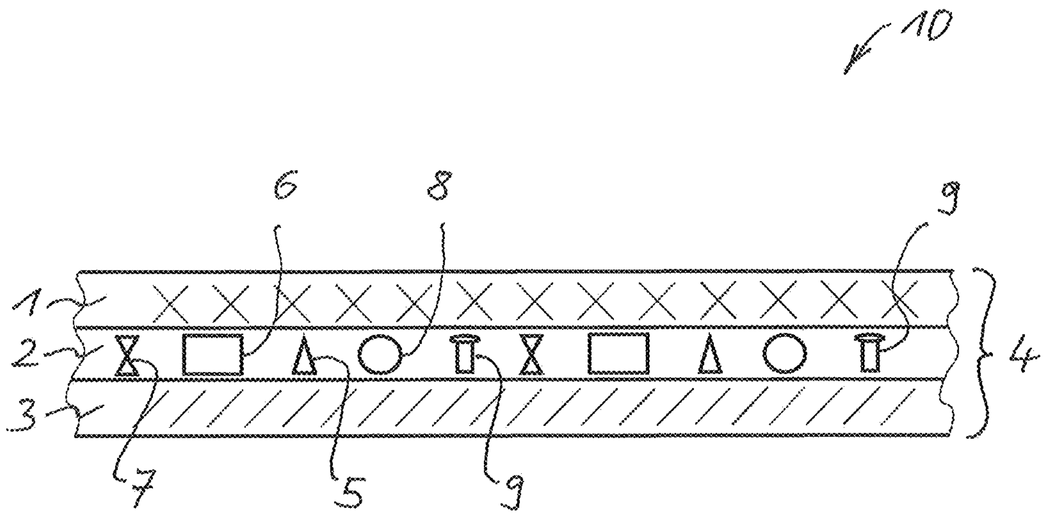
FIG. 3 Shows a further schematic representation of the structure with LEDs.

FIG. 3 shows a further embodiment of structure 10 with the upper layer 1, the middle layer 2, and the lower layer 3. The structure 10 forms the mat 4. The middle layer 2 comprises the various sensor elements 5, 6, 7, the heating elements 8, and light emitting diodes 9. The LEDs 9 are arranged within the middle layer 2 but could also be arranged separately on or within another layer. All elements have connections to the outside (not shown).

The LEDs 9 create light effects which guide a patient on the mat 4 for exact positioning. The LEDs 9 can also make an application or the device more attractive. The LEDs 9 can for example guide a user on the first lay down or the correct positioning of an arm or leg. By indications of LED signals, the users can be given instructions, e.g. where to move an arm or when an application has finished.

Figure 4:
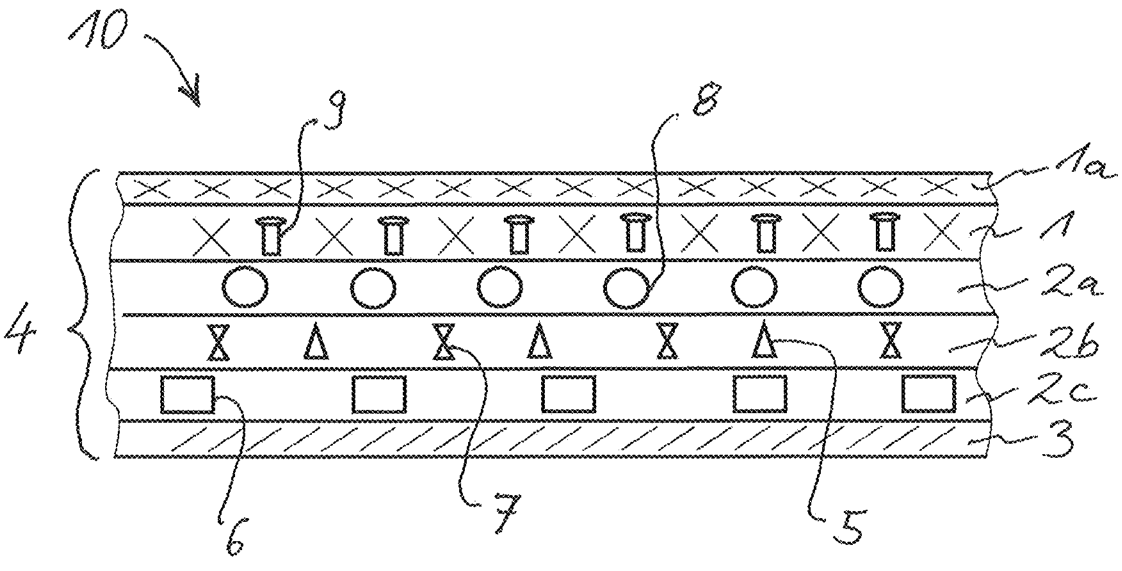
FIG. 4 Shows a schematic representation of another structure with multiple layers.

FIG. 4 shows a further embodiment of structure 10 with multiple layers. The structure 10 forms the mat 4 with at least five layers. The structure 10 comprises a top layer 1*a* with a protective coating, the upper layer 1, a third layer 2*a*, a fourth layer 2*b*, a fifth layer 2*c* and the lower layer 3. The LEDs 9 are here arranged at the upper layer 1 in order to allow a direct light emission towards the reclining surface though the top layer 1 with the protective coating. The third layer 2*a* comprises the heating elements 8. The fourth layer 2*b* comprises two sensor elements 5, 7, namely the position sensors 5 and the temperature sensors 7. Underneath, the pressure sensors 6 are arranged within the fifth layer 2*c*. Finally, the lower layer 3 is located at the bottom of the stack. In general, any kind of combination of the various elements and layers is possible. It might be advantageous to have certain sensors and/or elements in one layer whereas other sensors and/or elements are in a separate layer. An advanced manufacturing process may even allow to arrange all elements in one layer such that a thin, but robust mat 4 can be provided.

Figure 5:
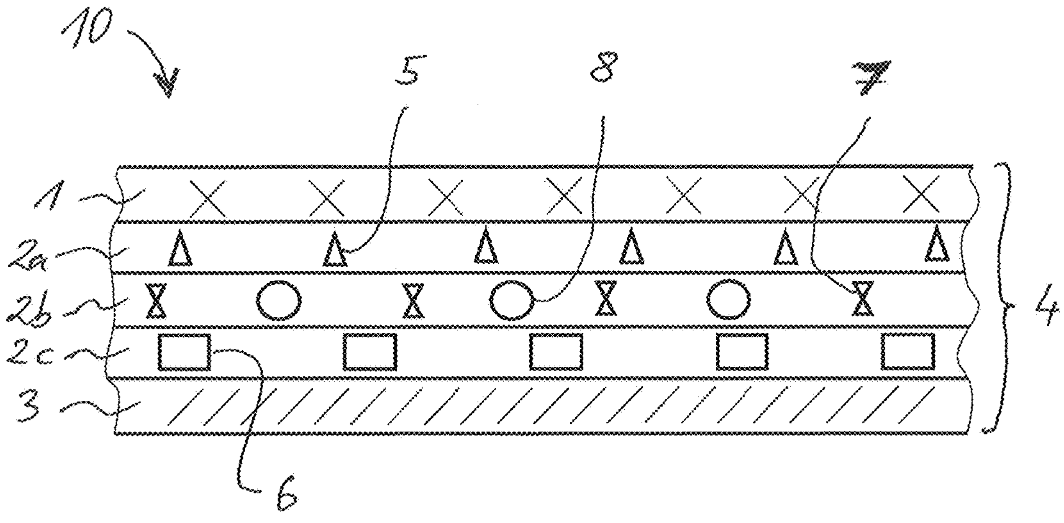
FIG. 5 Shows a schematic representation of a further structure with multiple layers.

FIG. 5 shows yet a further embodiment of structure 10 with multiple layers. The structure 10 with five layers forming the mat 4. The structure 10 comprises the upper layer 1, a second layer 2*a*, a third layer 2*b*, a fourth layer 2*c* and the lower layer 3 as the fifth layer. No LEDs are integrated. The upper layer 1 is a protection layer to the surface on which a patient will be positioned. The second layer 2*a* comprises the position sensors 5 for precise detection of the patient. The third layer 2*b* comprises two components 7, 8; the temperature sensors 7 and the heating elements 8 are arranged within the same layer. It might be advantageous for the manufacturing process to have the temperature sensor 7 and the heating elements 8 in the same layer. Below the third layer 2*b*, the pressure sensors 6 are arranged within the fourth layer 2*c*. The lower layer 3 consists of a water-resistant film that is explained in more detail below.

Figure 6:
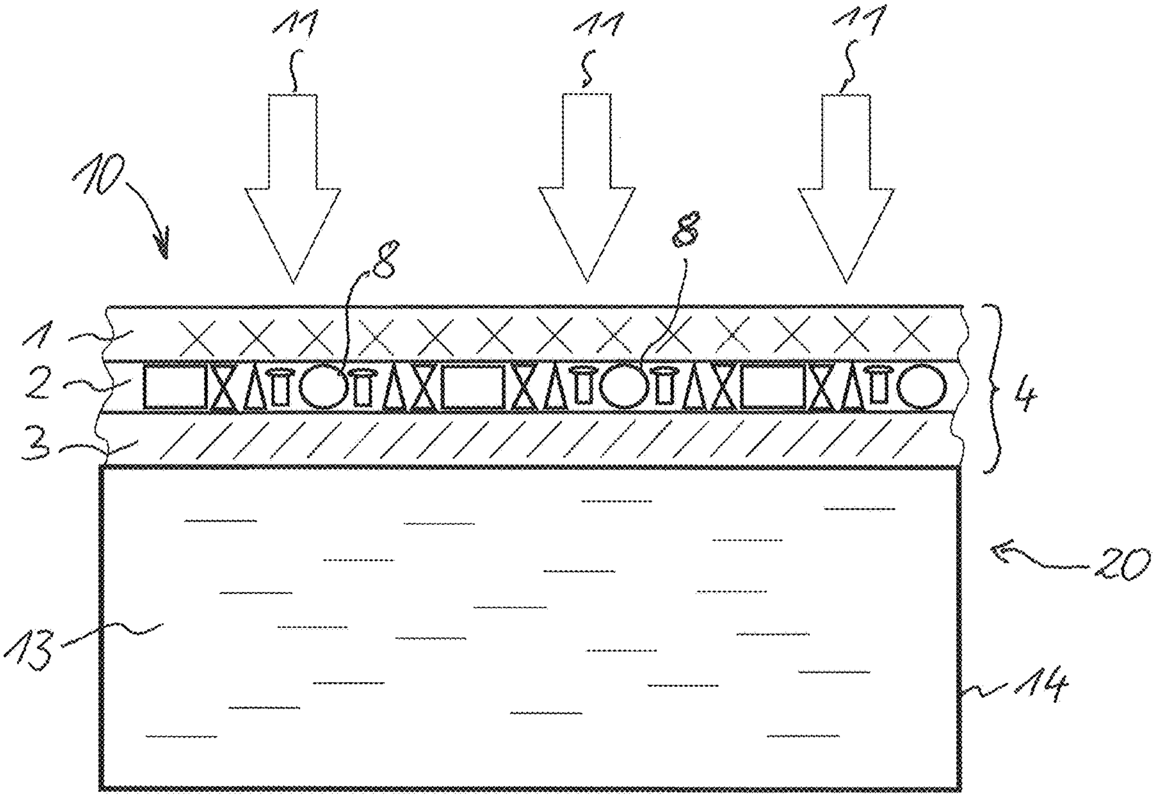
FIG. 6 Shows a schematic representation of a hydromassage device.

FIG. 6 shows a cross-section of a hydromassage device 20. In this embodiment the structure 10 comprises the upper layer 1, the middle layer 2, and the lower layer 3. Impacting first forces 11 are created from the top by a patient (not shown) on the mat 4. The lower layer 3 of the mat 4 is in direct contact with water 13 that is contained in a frame 14. The structure 10 is substantially horizontal as the mat 4 is on top of the water 13. The lower layer 3 has an insulating coating. This material is waterproof in order to not allow the other layers to become wet or effected by the water 13. The water 13 is arranged in a tank that is located within the frame 14. It is particularly advantageous that the water 13 in the tank does not need to be heated for comfort. This reduces energy. The heating is enabled directly within the mat 4 through the heating elements 8 to about 20 to 40 degrees Celsius.

The tank is filled with over 300 litres of water. The pressure strength, massage type and areas can be individually controlled for each treatment by the patient, but also controlled fully automatically through a control unit as described with reference to FIG. 8 below. The hydromassage device 20 provides various massage types such as parallel massage, mirror image massage, circle massage, or parallel stroke massage. Further, massage areas are selectable or applied through detection such as shoulder and/or neck massage, whole body, back, lumbar area, legs, etc. The duration of an application is usually in a range up to 45 minutes. The intensities of the pressure can be individually selected, but with the help of the pressure sensor 6 the pressure can be controlled in an optimized way.

Figure 7:
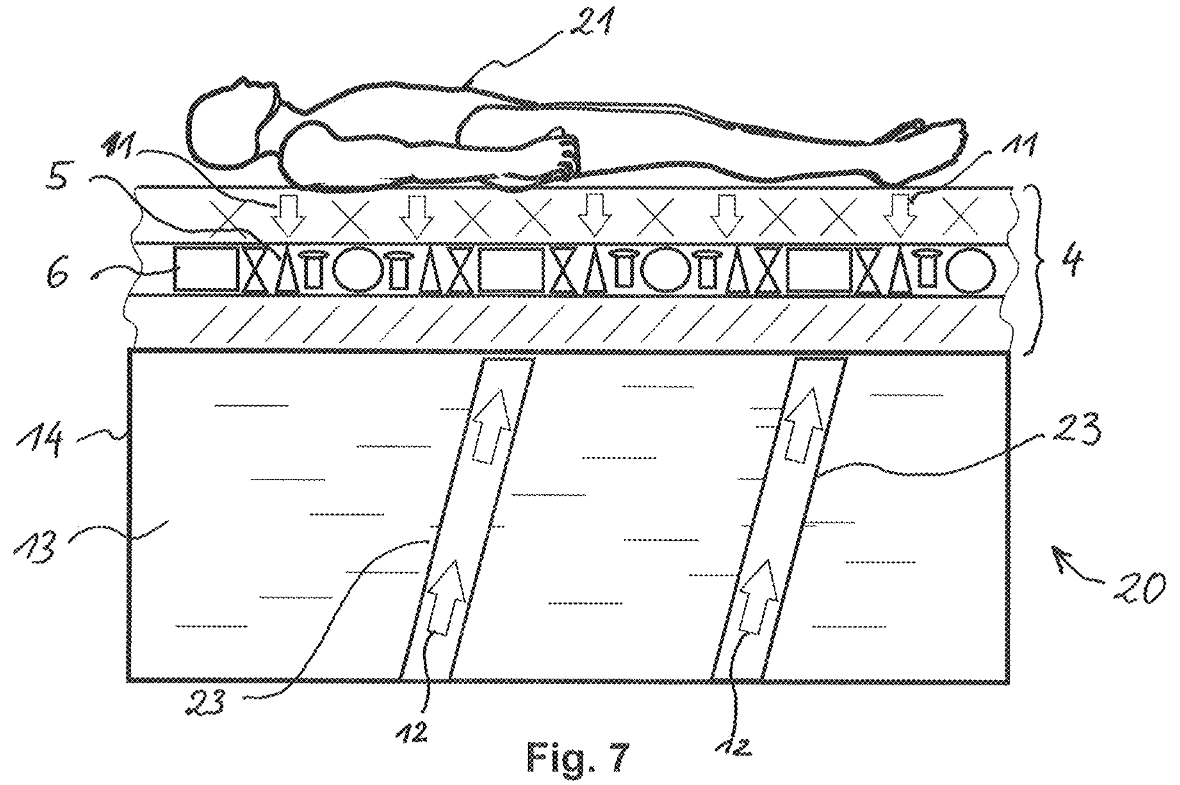
FIG. 7 Shows a schematic representation of a hydromassage device impacting forces from both sides.

FIG. 7 shows the hydromassage device 20 of FIG. 6 with two massage jets from the bottom exerting the second forces 12. Generally, from movable nozzles (not shown), the water jets 21 are pumped from below against the mat 4 on which a patient 21 is lying. The second forces 12 are detected by the pressure sensors 6. Electrical signals from the sensors 5, 6 are sent via electrical connections to the control unit or central processing unit. A treatment with defined pressure against areas is performed in response to the determined position of the patient through the position sensors 5.

Figure 8:
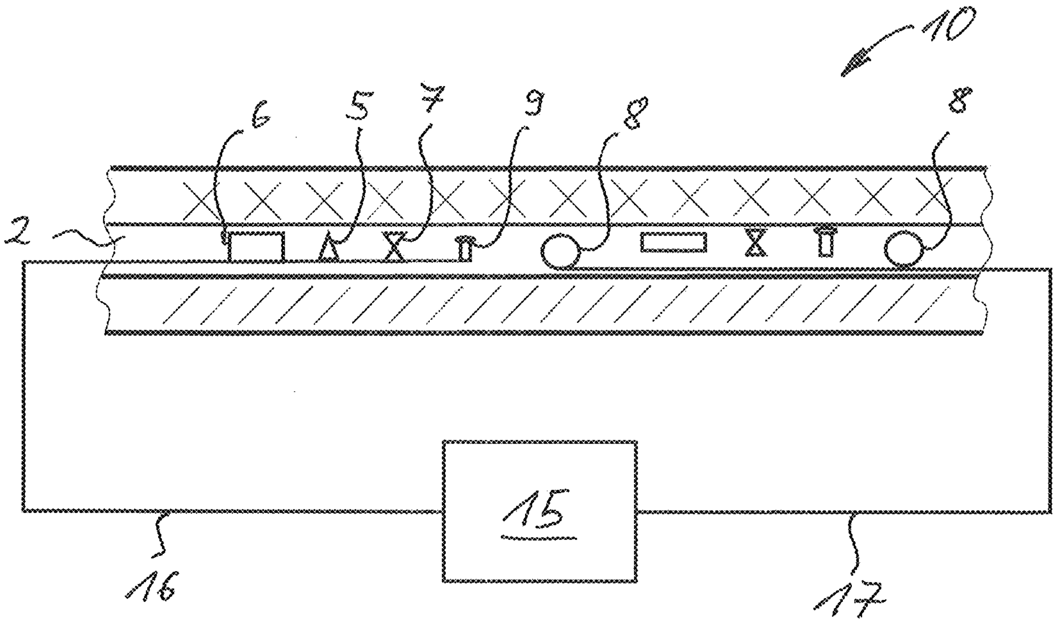
FIG. 8 Shows a schematic representation of a structure with electrical connections and a central control or processing unit.

FIG. 8 illustrates the structure 10 with the middle layer 2 and electrical connections 16, 17 to a control unit or central processing unit 15. First electrical connections 16 connect the sensor elements 5, 6, 7 to the central processing unit 15. The LEDs 9 are also connected through the first electrical connections 16 to the central processing unit 15. Second electrical connections 17 connect from the control unit 15 to the heating elements 8. The second electrical connections 16 are adapted to the current or power needs of the heating elements 8. That means in practice that the second electrical connections 17 are thicker than the first electrical connections 16.

The sensor elements 5, 6, 7 communicate with the central processing unit 15. The central processing unit 15 which can be connected to a network and further to the Internet enables various applications and treatments. As indicated above different massage types can be provided and various massage areas be addressed.

The position sensors 5 detect the position of user or certain parts of the body which require a treatment. The position sensors 5 might be adapted to detect the hardness of tissue or muscles. In response to that specific applications to certain areas or muscles with defined types and pressure are applied, all processed and controlled through the central processing unit 15. Software programs with specific code can be applied. The use of self-learning or adapting programs will result in more optimized applications for the benefit of the patient who receives a treatment that is individually most suitable and not a standard program.

The pressure sensors 6 detect the jet pressure from below. The jet pressure, i.e. the intensity, and the movement of the jet are controlled by the control or central processing unit 15. Based on the detected body contour of the patient a treatment program is applied that is most effective to the patient. With the help of the pressure sensors 6 the pressure intensity can be controlled in an optimized way.

The position sensors 5 and pressure sensors 6 can be realized by piezoelectric sensors. Such piezoelectric sensors use the piezoelectric effect to measure changes in pressure, acceleration, strain, or force by converting them to an electrical charge. Piezoelectric sensors do not require any power to continuously monitor an environment. They offer stable and repeatable accurate electrical output. With such sensors also the weight of a patient can be determined. Based on that, the jet pressure might be adapted.

The temperature sensors 7 help to determine and measure the temperature at the middle layer 2. The temperature sensors 7 deliver an electrical signal as a measure of the temperature and could be arranged within any other layer but are arranged where the temperature is detectable in an optimal way. The temperature sensors 7 send electrical signals via the first electrical connections 16 to the control or central processing unit 15 for processing. The heating elements 8 are heated through respective power applied to the second electrical connections 17. The heating and cooling process is controlled and adapted by the control or central processing unit 15. That means based on the detected and measured temperature the heating elements 8 are activated to heat up the structure 10.

Figure 9:
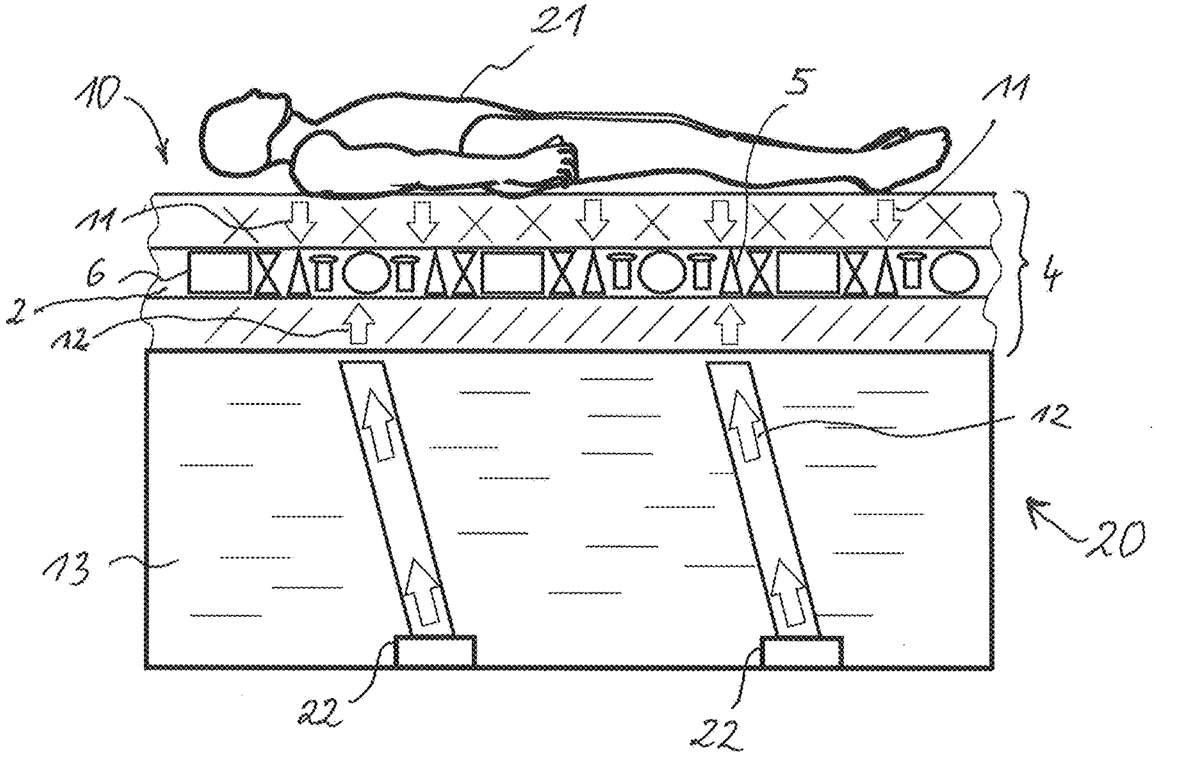
FIG. 9 Shows a schematic representation of a hydromassage device with a patient on the structure.

FIG. 9 shows a schematic representation of a hydromassage or jet device 20 with a user 21 on the structure 10. As illustrated in the figure the user or patient 21 reclines on the mat 4 and enjoys a therapeutic application in the form of a water jet massage through impacting forces, the second forces 12, created through nozzles 22. The patient 21 himself creates certain pressure from the top whereby the resulting first forces 11 are detected and measured by the position sensors 5. The structure 10 is arranged between the body of the patient or user 21 and the impacting force 12. The pressure sensors 6 detect the jet pressure as the second forces 12 from below. The jet pressure, the movement of the jet, and the temperature are controlled by the control or central processing unit 15 (not shown in the figure). Based on a program and the detected body contour of the patient a treatment is applied that is most effective for the patient.

As indicated above the structure 10 can be a fabric into which different fibres are woven. The structure 10 for therapeutic applications is produced by weaving a plurality of fibres into the fabric, adding sensor elements 5, 6, 7 and heating elements 8 between the fibres to form at least one layer 2. The layer 2 is affectable with the first force 11 from one side, usually form the top, and the second force 12 from the other side, usually from the bottom. The mat 4 can be realized as an e-textile combining electronic devices such as the sensor elements 5, 6, 7 and heating elements 8 with textiles. The electronics with active and passive elements are integrated directly into the textile substrates. The conducting textile weaves are connected to the control or central processing unit 15. Printing techniques could be applied to create the sensor elements 5, 6, 7 and heating elements 8.

Figure 10:
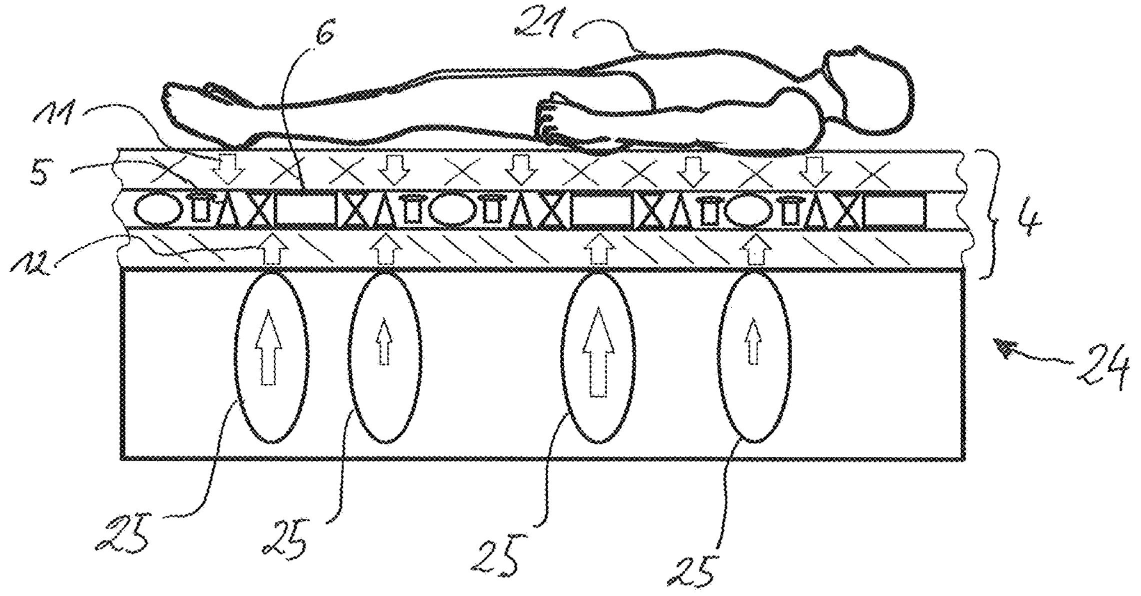
FIG. 10 Shows a schematic representation of a massage device with a patient on the structure.

FIG. 10 shows a schematic representation of a massage device 24 with a patient 21 on the structure 10. The massage device 24 comprises moving drums 25. As illustrated in the figure the patient 21 in positioned on the mat 4 horizontally and enjoys a therapeutic application in the form of a massage through impacting forces, the second forces 12, created through the moving drums 25. The patient 21 himself creates certain pressure from the top whereby the resulting first forces 11 are detected and measured by the position sensors 5. The structure 10 is arranged between the body of the patient or user 21 and the impacting force 12. The pressure sensors 6 detect the pressure as the second forces 12 from the moving drums 25. The pressure, the movement of the drums 25, and the temperature are controlled by the control or central processing unit 15 (not shown in the figure). Based on a program and the detected body contour of the patient a treatment is applied that is most effective for the patient. The arrangement of the mat 4 is flexible, depending form where the second forces 12 are applied. The means the mat 4 can also be applied if the patient 21 is sitting, standing, or in an inclined position.

The embodiments described and shown can be combined with each other and are intended to illustrate one or more ways to practice and implement the present disclosure. It is further noted that the foregoing description of the specific embodiments of the subject matter disclosed herein has been presented for purposes of illustration and description and is not intended to limit the scope of the subject matter set forth herein. It is fully contemplated that other various embodiments, modifications and applications will become apparent to those of ordinary skill in the art from the foregoing description and accompanying drawings. Thus, such other embodiments, modifications, and applications are intended to fall within the scope of the following appended claims. Further, those of ordinary skill in the art will appreciate that the embodiments, modifications, and applications that have been described herein are in the context of particular environment, and the subject matter set forth herein is not limited thereto, but can be beneficially applied in any number of other manners, environments and purposes. Accordingly, the claims set forth below should be construed in view of the full breadth of the novel features and techniques as disclosed herein.

LIST OF REFERENCES

1 upper layer
2 middle layer
3 lower layer
4 mat
5, 6, 7 sensor elements
 5 position sensors
 6 pressure sensors
 7 temperature sensors
8 heating elements
9 light emitting diodes (LEDs)
10 structure
11 first force
12 second force
13 water
14 frame
15 control or central processing unit
16 first electrical connections
17 second electrical connections
20 hydromassage device
21 patient or user
22 nozzles
23 water jet
24 massage device
25 moving drum

The invention claimed is:

1. A structure for external hydromassage therapeutic applications with at least one moveable jet comprising:

at least one layer comprising:

a fabric into which different fibers are woven together, and a plurality of sensor elements integrated within the different fibers of the fabric and distributed throughout the at least one layer, wherein the pressure sensor elements are arranged to detect and measure a plurality of first pressure forces applied to a plurality of positions on the at least one layer from one side and a plurality of second pressure forces applied to a plurality of positions on the at least one layer from an opposite side, an upper layer comprising the fabric into which different fibers are woven together, a lower layer comprising the fabric into which different fibers are woven together, wherein the structure is arranged as an area of support for receiving at least one body part of a user on the one side and for receiving impact forces from the at least one moveable jet from the opposite side, and wherein the at least one layer is sandwiched between and abuts against the upper layer and the lower layer.

2. The structure of claim 1, wherein the at least one layer further comprises heating elements.

3. The structure according to claim 1, wherein the sensor elements comprise position sensors for detecting user features.

4. The structure according to claim 1, wherein the sensor elements comprise pressure sensors for detecting impact forces.

5. The structure according to claim 1, wherein the sensor elements comprise temperature sensors for determining a temperature.

6. The structure according to claim 1, wherein the at least one layer comprises a plurality of layers and the sensor elements are arranged in the plurality of layers.

7. The structure according to claim 1, wherein at least one of the upper layer, the lower layer and the at least one layer comprises light emitting diodes configured to provide a plurality of different instructions to the user.

8. The structure according to claim 7, wherein the plurality of different instructions to the user are indicative of at least one of:

movement or change of position of the at least one body part on the area of support of the structure;

guiding the at least one body part into an exact position on the area of support of the structure;

certain progress of a therapeutic application; and an end of a therapeutic application.

9. The structure according to claim 1, further comprising electrical connections for electrical signals.

10. The structure according to claim 1, wherein the area of support on one the side of the structure is arranged to receive at least a body part of a user and the opposite side of the structure is arranged to be subjected to the second force being a jet pressure force provided by the at least one moveable jet.

11. The structure according to claim 1, wherein the lower layer comprises an elastic waterproof film.

12. A mat comprising a structure according to claim 1.

13. The structure of claim 1, wherein:

the plurality of first pressure forces are created by the at least one body part on the area of support of the structure; and the plurality of pressure sensors are configured to enable a determination of a size and contour of the at least one body part from measurements of the plurality of first pressure forces.

14. A hydromassage-device with a movable jet comprising a frame and the structure according to claim 1, the structure being configured to be arranged substantially horizontally such that the area of support on one side of the structure comprises a reclining surface for a patient.

15. A method for operating a hydromassage device comprising a structure according to claim 14, comprising the steps of:

a. providing a processing unit with sensor data indicative of a first force affecting a layer from one side that provides an area of support and with sensor data indicative of a second force affecting the layer from the opposite side;

b. providing at least one means for applying the second force to the layer, the at least one means being at least one moveable jet; and c. adapting the second force reflective of the sensor data indicative of the first force affecting the layer from the one side and the sensor data indicative of the second force affecting the layer from the opposite side.

16. The method according to claim 15, wherein the second force is a jet-pressure force created by the at least one moveable jet, in particular by at least one water jet with a treatment pressure.

17. The method according to claim 15, whereby the first force is created through a physical contact between a patient and the structure.

18. The method according to claim 15, whereby a body shape or size of a patient is identified by means of sensor data indicative of the first force, and, based on a predetermined therapy scheme, a respective program is applied, in particular whereby the adapting the second force comprises targeting at least one nozzle, from which the at least one moveable jet is pumped, to parts of a body of the patient based on the body shape or size identified.

19. The method according to claim 15, whereby the adapting comprises an adjusting and controlling of an intensity of the second force dependent on the sensor data indicative of the first force affecting the layer from the one side and the sensor data indicative of the second force affecting the layer from the opposite side.

20. The method according to claim 15, whereby the structure comprises temperature sensors for determining a temperature, the method comprising:

a. sensing a temperature by means of at least one of the temperature sensors in the structure, and b. controlling the temperature by means of heating elements controlled by the central processing unit.

21. The hydromassage device of claim 14 comprising a processing unit configured to receive sensor data from at least one of the sensor elements indicative of the first force affecting the at least one layer, the first force being as a result of a patient reclining on the reclining surface, and configured to receive sensor data from at least one of the sensor elements indicative of the second force affecting the at least one layer, the second force being a jet pressure force created by the at least one movable jet.

22. The hydromassage device of claim 21, wherein the processing unit is configured to identify a body shape or size of the patient by means of the sensor data indicative of the first force, and, based on a predetermined therapy scheme, adapt the second force by changing an intensity of the jet pressure force and/or by targeting at least one nozzle, from which the at least one moveable jet is pumped, to parts of a body of the patient, based on the identified body shape or size.

* * * * *